United States Patent
Ten Cate et al.

(10) Patent No.: US 11,298,099 B2
(45) Date of Patent: Apr. 12, 2022

(54) METHOD FOR CONTROLLING THE OPERATION OF A MEDICAL APPARATUS, OPERATING DEVICE, OPERATING SYSTEM, MEDICAL APPARATUS, COMPUTER PROGRAM AND ELECTRONICALLY READABLE DATA CARRIER

(71) Applicant: Siemens Healthcare GmbH, Erlangen (DE)

(72) Inventors: Gerben Ten Cate, Forchheim (DE); Robert Kagermeier, Nuremberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 20 days.

(21) Appl. No.: 17/041,662

(22) PCT Filed: Apr. 2, 2019

(86) PCT No.: PCT/EP2019/058298
§ 371 (c)(1),
(2) Date: Sep. 25, 2020

(87) PCT Pub. No.: WO2019/197222
PCT Pub. Date: Oct. 17, 2019

(65) Prior Publication Data
US 2021/0007701 A1   Jan. 14, 2021

(30) Foreign Application Priority Data

Apr. 11, 2018 (DE) ..................... 10 2018 205 496.7

(51) Int. Cl.
*G16H 40/67* (2018.01)
*A61B 6/00* (2006.01)
(Continued)

(52) U.S. Cl.
CPC ............ *A61B 6/548* (2013.01); *G06F 3/0484* (2013.01); *G06F 3/0488* (2013.01); *G06N 20/00* (2019.01);
(Continued)

(58) Field of Classification Search
CPC ...................................... G16H 40/67
(Continued)

(56) References Cited

U.S. PATENT DOCUMENTS 8,114,063 B2 *  2/2012  Sacco ..................... G16H 20/40
                                               604/523
9,523,750 B2 * 12/2016  Senegas ............... G01R 33/546
(Continued)

FOREIGN PATENT DOCUMENTS

DE   102008062032 A1   7/2010
DE   102013219194 A1   3/2015
(Continued)

OTHER PUBLICATIONS

Tony Fitzpatrick, "Ultrasound imaging now possible with a smartphone" available online at <https://source.wustl.edu/2009/04/ultrasound-imaging-now-possible-with-a-smartphone/>, published on Apr. 20, 2009, 4 pages. (Year: 2009).*
(Continued)

*Primary Examiner* — Reza Nabi
(74) *Attorney, Agent, or Firm* — Harness, Dickey & Pierce, P.L.C.

(57) ABSTRACT

A method is for controlling the operation of a medical apparatus. The method includes determining input data including patient data relating to a patient, operational status data relating to operational status of the medical apparatus, position data describing position of at least one of the wireless, handheld mobile operating device and the patient in relation to the medical apparatus, and workflow data
(Continued)

describing at least one of a medical apparatus workflow and a current position in the medical apparatus workflow; determining, using an artificial intelligence analysis algorithm, at least one of a subsequent operating action of an operator of the wireless, handheld mobile operating device and prediction data describing an item of information needed next by the operator; and at least one of selecting and adapting a user interface to be displayed on the touch screen, based upon the prediction data and displaying the user interface on the touch screen.

17 Claims, 5 Drawing Sheets

(51) Int. Cl.
| | | |
|---|---|---|
| G16H 40/20 | (2018.01) | |
| G16H 30/20 | (2018.01) | |
| G16H 50/20 | (2018.01) | |
| G06N 20/00 | (2019.01) | |
| G06F 3/0484 | (2022.01) | |
| G06F 3/0488 | (2022.01) | |

(52) U.S. Cl.
CPC ............. *G16H 30/20* (2018.01); *G16H 40/20* (2018.01); *G16H 40/67* (2018.01); *G16H 50/20* (2018.01)

(58) Field of Classification Search
USPC ......................................................... 715/740
See application file for complete search history.

(56) References Cited

U.S. PATENT DOCUMENTS

| | | | | |
|---|---|---|---|---|
| 10,854,335 | B2* | 12/2020 | Tang ...................... | G16H 50/20 |
| 2008/0082362 | A1* | 4/2008 | Haider ................... | G16H 70/60 |
| | | | | 705/2 |
| 2010/0131294 | A1* | 5/2010 | Venon ..................... | G16H 30/40 |
| | | | | 705/3 |
| 2011/0122068 | A1* | 5/2011 | Venon ................... | G06T 19/003 |
| | | | | 345/169 |
| 2012/0042039 | A1* | 2/2012 | Mark ..................... | G16H 40/20 |
| | | | | 709/217 |
| 2015/0142457 | A1* | 5/2015 | Marshall ................ | G16H 50/50 |
| | | | | 705/2 |
| 2016/0242716 | A1 | 8/2016 | Dinse et al. | |
| 2017/0372009 | A1* | 12/2017 | Sanyal .................. | A61B 5/6803 |
| 2018/0070882 | A1* | 3/2018 | Schneider ............ | A61B 5/0046 |
| 2018/0078222 | A1* | 3/2018 | Boettger ................ | G16H 40/63 |
| 2018/0206818 | A1* | 7/2018 | Dirauf .................... | G16H 40/67 |
| 2018/0211730 | A1* | 7/2018 | Slepian .................. | G16H 40/60 |
| 2018/0294052 | A1* | 10/2018 | Fishman ............ | G06Q 10/1095 |
| 2018/0366222 | A1* | 12/2018 | Tang ........................ | G06N 5/04 |
| 2019/0150876 | A1* | 5/2019 | Kagermeier ............ | A61B 6/06 |
| 2019/0358633 | A1* | 11/2019 | Collins ............... | B01L 3/50273 |
| 2020/0004583 | A1* | 1/2020 | Kelly ..................... | G06N 20/00 |
| 2020/0013501 | A1* | 1/2020 | Page ...................... | G16H 40/40 |
| 2020/0075157 | A1* | 3/2020 | Monheiser ............. | G16H 70/20 |
| 2020/0185102 | A1* | 6/2020 | Leventhal .............. | G16H 50/20 |
| 2020/0203010 | A1* | 6/2020 | Durlach ................... | A61G 7/00 |
| 2020/0312452 | A1* | 10/2020 | Durlach ................. | A61G 7/012 |
| 2021/0007701 | A1* | 1/2021 | Ten Cate .............. | G06F 3/0484 |
| 2021/0272690 | A1* | 9/2021 | Behuria ................. | A61B 90/36 |
| 2021/0358619 | A1* | 11/2021 | Vu ........................ | A61B 5/6898 |

FOREIGN PATENT DOCUMENTS

| | | |
|---|---|---|
| DE | 102013219195 A1 | 3/2015 |
| DE | 102013219145 A1 | 4/2015 |
| DE | 102017217128 A1 | 3/2019 |
| EP | 1527799 A2 | 5/2005 |
| EP | 3352030 A1 | 7/2018 |
| EP | 3486915 A1 | 5/2019 |
| WO | WO-2007/133667 A2 | 11/2007 |
| WO | WO 2016001647 A1 | 1/2016 |

OTHER PUBLICATIONS

International Search Report PCT/ISA/210 for International Application No. PCT/EP2019/058298 dated Jul. 3, 2019.
Written Opinion of the International Searching Authority PCT/ISA/237 for International Application No. PCT/EP2019/058298 dated Jul. 3, 2019.
German Office Action for German Application No. 10 2018 205 496.7 dated Nov. 15, 2018.

\* cited by examiner

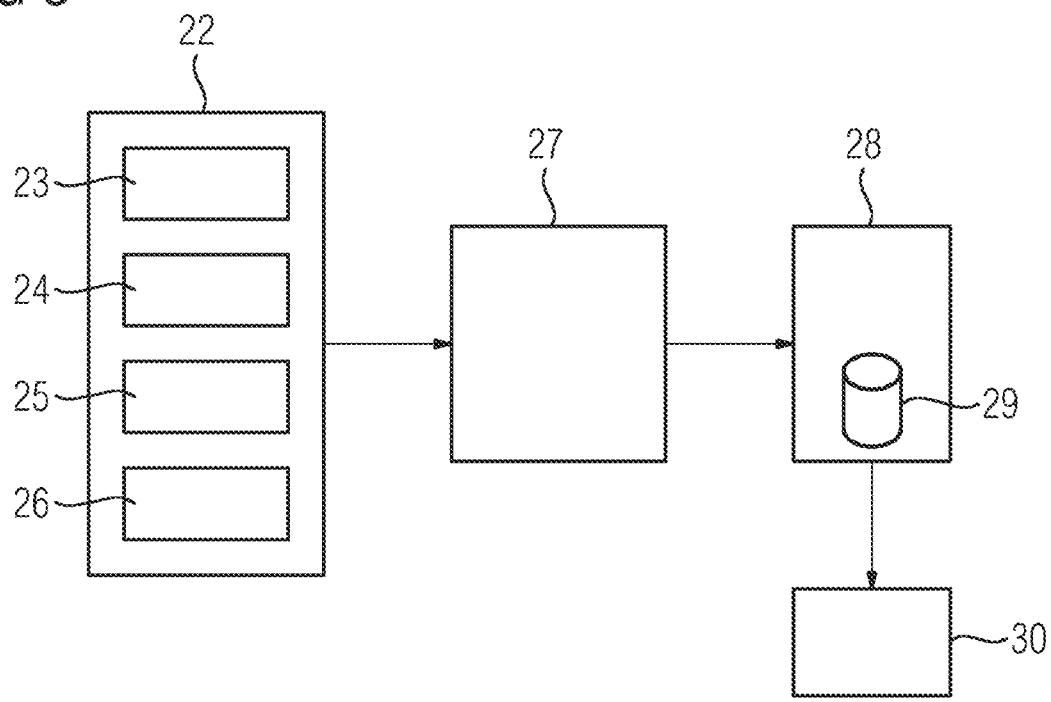
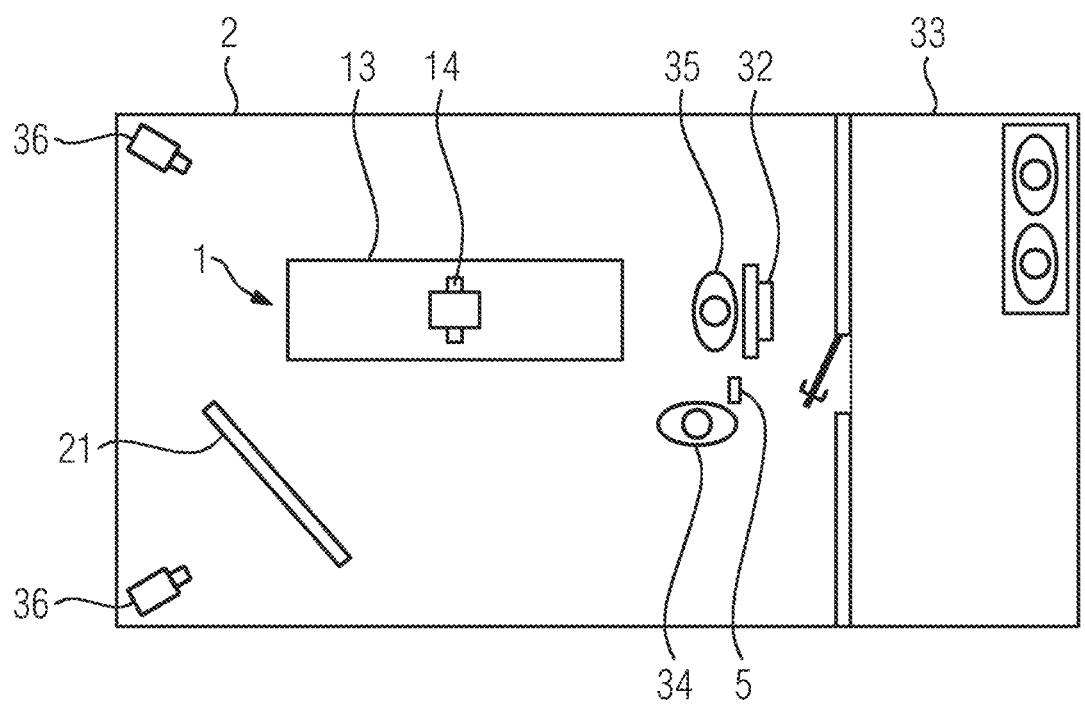

METHOD FOR CONTROLLING THE OPERATION OF A MEDICAL APPARATUS, OPERATING DEVICE, OPERATING SYSTEM, MEDICAL APPARATUS, COMPUTER PROGRAM AND ELECTRONICALLY READABLE DATA CARRIER

PRIORITY STATEMENT

This application is the national phase under 35 U.S.C. § 371 of PCT International Application No. PCT/EP2019/058298 which has an International filing date of Apr. 2, 2019, which designated the United States of America and which claims priority to German application no. 10 2018 205 496.7 filed Apr. 11, 2018, the entire contents of each of which are hereby incorporated by reference herein, in their entirety and for all purposes.

FIELD

An embodiment of the disclosure generally relates to a method for controlling the operation of a medical apparatus, in particular, an imaging apparatus, whereby a wireless, handheld mobile operating device with a touch screen is used and a plurality of functions of a medical apparatus workflow are realized via the operating device for an examination and/or treatment process of a patient with the medical apparatus. In addition, an embodiment of the disclosure generally relates to an operating device, an operating system, a medical apparatus, a computer program and an electronically readable data carrier.

BACKGROUND

Modern medical apparatuses, that is, in particular large medical technology systems for examining and/or treating patients are growing in the complexity of their equipment and operation. Therefore, the operation of a medical diagnostic/therapy system represents a challenge in the realization thereof with regard to usability and ergonomics. A simple and intuitive operation is thereby desirable, but in conventionally known medical apparatuses, it is often insufficiently implemented.

For example, medical examination apparatuses, in particular, X-ray apparatuses are known which have a plurality of operating locations with different operating apparatuses for their operation. For example, a screen console with a keyboard and mouse can be provided in an anteroom of the room in which the medical apparatus is arranged, wherein furthermore, a touch screen can be provided as an input apparatus, for example, on a ceiling-mounted X-ray radiator, and/or one or more close-range operating units (wire-bound or wireless) can be provided. During the operation of such a medical apparatus, the operator therefore changes the operating locations and the operating apparatuses multiple times, which is relatively non-ergonomic.

Solutions proposed in the prior art for simplifying the operation relate mostly to particular of these operating apparatuses and their actual implementation for the realization of specific functions. Thus, for example, in DE 10 2013 219 195 A1, a remote operation device and a method for controlling a device with at least one degree of freedom of movement is proposed with which a movable component of a medical apparatus can be controlled on the basis of movements of the remote operation device, wherein the transmission ratio for a coarse positioning and a fine positioning can be exchanged. DE 10 2013 219 194 A1 and DE 10 2013 219 145 A1 relate to the use of control elements that can be configured, in particular, as joysticks, wherein additionally selection elements are provided for selection of the movable element that is to be controlled of a medical system, that is, of a medical apparatus, or a perspective-related adaptation takes place.

It has recently also been proposed to provide mobile, hand-held operating devices with a touch screen, in particular, commercially available smart devices, for operating medical apparatuses. The subsequently published patent applications DE 10 2017 217 128.6 and EP 17152779.9 relate to different aspects of an expansion unit that is portable or connectable to a mobile terminal, in which expansion unit safety-related functionalities, that is, such as fulfil safety requirements can be partially outsourced in order to prevent, as far as possible, the realization of the safety requirements within the commercially available smart device. The expansion unit can be coupled mechanically and/or by data technology to the smart device, in particular, in the form of an "expansion shell".

In the subsequently published EP 17202205.5, an integral operating approach is proposed for a method of a related type in that with the operating device for an examination and/or treatment process on a patient with the medical apparatus at least the following functions of a medical apparatus workflow implementing the process are realized by way of the operating device:

acquiring patient data of the patient from an acquisition-user interface, selecting, via a selection user interface, a medical technology protocol containing operating parameters which is to be carried out for the acquired patient, adjusting remotely-adjustable components of the medical apparatus to the patient positioned in the medical apparatus and the medical technology protocol to be carried out using an adjustment user interface, triggering the medical technology procedure with the patient positioned and the components adjusted in a triggering user interface.

Through the use of an efficient, portable, small-format touch display unit as the operating device, in particular, a smart device, it is therefore enabled therein to implement the complete medical apparatus workflow on a single user device, so that an ergonomic, simple, intuitive and complete operation of a medical apparatus, and therefore a medical technology system, is achieved. The implementation of the operating functions and processes on a portable, wireless, mobile operating device enables a complete, simple and intuitive operation of a medical apparatus, in particular, an imaging apparatus close to the operator. It is therein also proposed to acquire and possibly also to track the position of the operating device, at least temporarily, in particular, continuously in the form of position data, wherein at least one function and/or at least one user interface of the medical apparatus workflow can be adapted dependent upon the position data.

With an expanded functionality of an operating device of this type, the effort for finding the correct user interface and functionalities also increases.

SUMMARY

At least one embodiment of the invention provides a possibility that is designed to be further simplifying and more intuitive for the operation of a medical apparatus.

Embodiments of the invention are directed to a method, an operating device, an operating system, a medical apparatus, a computer program and an electronically readable data carrier. Advantageous developments are disclosed in the claims.

In a method according to at least one embodiment of the invention for controlling the operation of a medical apparatus in which a wireless, handheld, mobile operating device with a touch screen is used and a plurality of functions of a medical apparatus workflow are realized via the operating device for an examination and/or treatment process of a patient with the medical apparatus, for the determination of a user interface to be displayed, the method comprises:

input data describing a current operational situation comprising patient data regarding the patient, operational status data regarding the operational status of the medical apparatus, position data describing the position of the operating device and/or of a patient relative to the medical apparatus and workflow data describing the medical apparatus workflow and/or a current position in the medical apparatus workflow, are determined, via an artificial intelligence analysis algorithm, a subsequent operating action by the operator and/or an item of prediction data describing information needed next by the operator is determined, and the user interface to be displayed is selected and/or adapted dependent upon the prediction data and is then displayed.

In addition to the method, at least one embodiment of the invention also relates to a wireless handheld, mobile operating device for controlling a medical apparatus, having a touch screen and a control unit configured for carrying out the method according to the invention. The execution of the method according to the invention can, however, also be distributed, so that the invention also relates to an operating system for controlling the operation of a medical apparatus, having a wireless handheld, mobile operating device with a touch screen and a control apparatus comprising a control unit of the operating device and a control unit of the medical apparatus configured for carrying out the method according to the invention. All the disclosures relating to the method according to embodiments of the invention can be transferred similarly to the operating device according to embodiments of the invention and the operating system according to embodiments of the invention, so that the aforementioned advantages can also be obtained with this.

Finally, at least one embodiment of the invention also relates to a medical apparatus, in particular, an imaging apparatus having an operating device according to at least one embodiment of the invention or an operating system according to at least one embodiment of the invention. The above disclosures can also naturally be applied to the medical apparatus.

A computer program according to at least one embodiment of the invention is, for example, directly loadable into a memory store of a control unit of an operating device or a control apparatus of an operating system and has program segments in order to carry out the steps of a method according to at least one embodiment of the invention when the computer program is executed in the control unit of the operating device or the control apparatus of the operating system.

The computer program can be stored on an electronically readable data carrier according to at least one embodiment of the invention which therefore comprises electronically readable control information stored thereon, which comprises at least one computer program according to at least one embodiment of the invention and is configured such that, on use of the data carrier in a control unit of an operating device or a control apparatus of an operating system, the control information carries out a method according to at least one embodiment of the invention. The electronically readable data carrier can be, in particular, a non-transient data carrier, for example, a CD-ROM.

BRIEF DESCRIPTION OF THE DRAWINGS

Further advantages and details of the present invention are disclosed in the following description of example embodiments and by reference to the drawings, in which:

FIG. 3 is a sketch to illustrate an example embodiment of the method according to the invention, FIG. 4 is a first operational situation.

DETAILED DESCRIPTION OF THE EXAMPLE EMBODIMENTS

Figure 1:
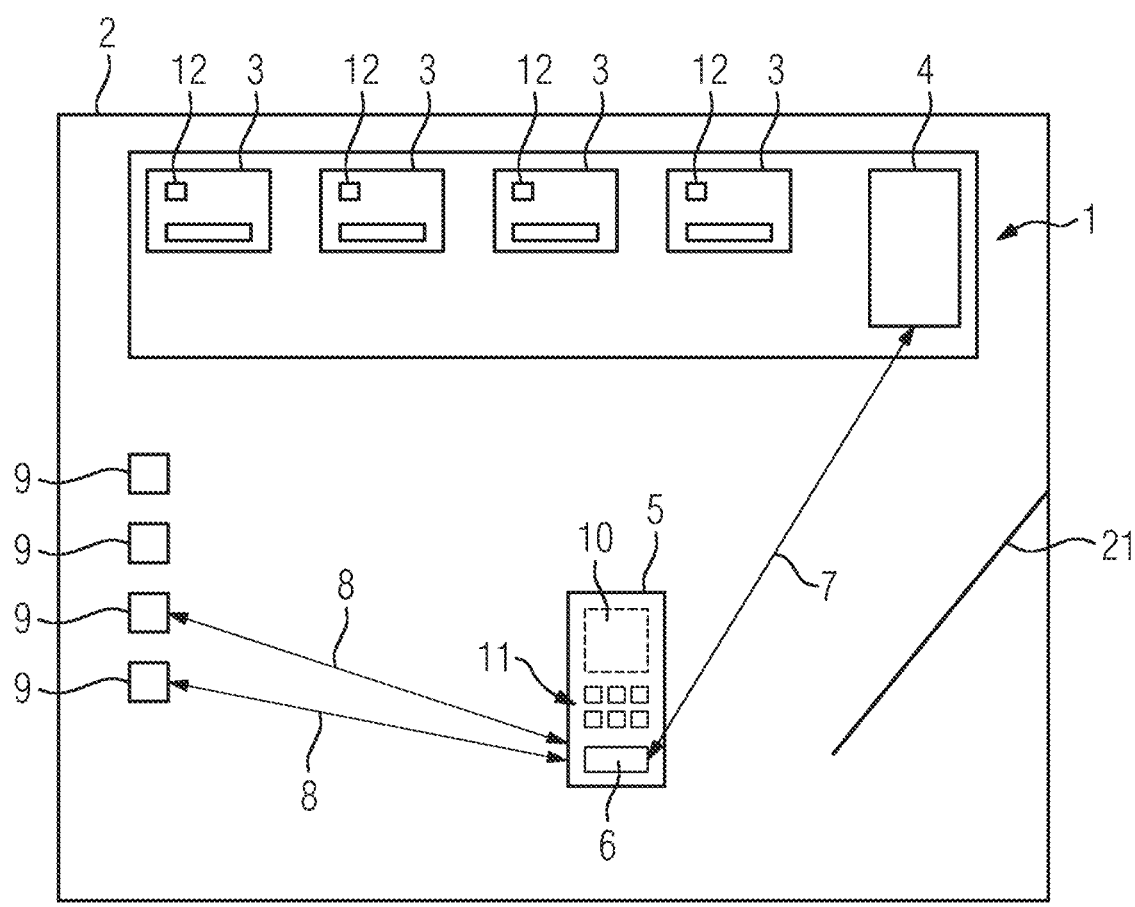
FIG. 1 is a sketch of the principle of components of a medical apparatus according to the invention.

In a method according to at least one embodiment of the invention for controlling the operation of a medical apparatus in which a wireless, handheld, mobile operating device with a touch screen is used and a plurality of functions of a medical apparatus workflow are realized via the operating device for an examination and/or treatment process of a patient with the medical apparatus, for the determination of a user interface to be displayed, the method comprises:

input data describing a current operational situation comprising patient data regarding the patient, operational status data regarding the operational status of the medical apparatus, position data describing the position of the operating device and/or of a patient relative to the medical apparatus and workflow data describing the medical apparatus workflow and/or a current position in the medical apparatus workflow, are determined, via an artificial intelligence analysis algorithm, a subsequent operating action by the operator and/or an item of prediction data describing information needed next by the operator is determined, and the user interface to be displayed is selected and/or adapted dependent upon the prediction data and is then displayed.

It is therefore proposed to solve the problem of finding while selecting the correct functionality via an intelligent, adaptive user interface on the touch screen of the operating device. On the basis of input data describing the operational situation, in particular, position data and system preconditions, a context-specific functionality is provided to the operator which he or she needs at this specific moment at this specific location. For this purpose, an artificial intelligence analysis algorithm is used which, in particular, on the basis of training data, can be assembled in a targeted manner or which can preferably be derived from operating procedures of the past, is in a position to predict which operating action the operator is most likely to carry out next or which information the operator is most likely to need for the next step. Dependent upon correspondingly arising prediction data, a user interface which is displayed on the touch screen is selected and/or adapted in order to enable this predicted operating action or to represent the correspondingly required information.

Varied input data for describing the operational situation is thereby useful and is utilized in the context of the present invention. At least a part of the input data can already be present as information in the medical apparatus or in the environment thereof, for example, in an information system that is used. An example thereof is patient data which is usually acquired at the start of the examination manually and/or automatically on the basis of a patient identification, which takes place at the start of the medical apparatus workflow. Patient data can define, for example, the age, sex and noteworthy physical limitations of the patient, the height, the weight and suchlike. Frequently, such patient data is already available, as previously mentioned, at least partially in the information systems that are used by the medical apparatus, for example, in a hospital information system (HIS) and/or in a radiology information system (RIS). Access to electronic patient files is also conceivable. Further information can also be obtained from the medical apparatus, an operating system realized with the operating device and/or an information system that is used, in particular, information regarding the examination and/or treatment process to be carried out, regarding components of the medical apparatus to be used, examination and/or treatment protocols to be used, regarding the current position in the workflow and other workflow data. The medical apparatus can also provide operational status data regarding the operational status of the medical apparatus itself, for example, the positions and/or adjustments and/or operating parameters of different components which can be present in a control unit of the medical apparatus.

Further sources of input data are different types of sensors that are provided in the environment of the medical apparatus. Noteworthy herein are, firstly, sensors of a position-determining system for the operating device itself, wherein the localization can take place using, for example, Bluetooth low energy (BLE), visual light communication (VLC) and/or optical tracking, which is described in greater detail below. Also noteworthy are cameras arranged, in particular, in an examination and/or treatment room, which can provide not only information regarding the patient and to supply it to the operator, but also regarding components of the medical apparatus, in particular, to check and/or to enhance operational status data provided by the medical apparatus itself. It should also be noted thereby at this point that position data can include not only positional information, but also orientation information.

Thereby, in the context of at least one embodiment of the present invention, input data describing the current operating state as specifically as possible is drawn from a plurality of sources, in particular, comprising sensors and/or the medical apparatus and/or an information system that is used in order to achieve as extensive a "situation awareness" as possible for the analysis algorithm. The analysis algorithm itself ultimately represents a cognitive system which, by way of cognitive steps, converts the operational situation described by the input data into a prediction which underlies a subsequent decision, specifically the selection and/or adaptation of the user interface. As a result, a workflow-specific and situation context-specific user interface on the basis of input data and input data analysis (prediction) is offered to the operator in order to enable the most probable next interaction of the user and/or the output of required information.

In summary, the operator is hereby enabled to work more rapidly with a mobile, handheld operating device with a touch screen which provides an expanded functionality so that the overall efficiency of the workflow is increased. Despite an increased number of functions which can be realized via the operating device, an intuitively-operated "thinking" mode of operation is provided for the operator, which increases its acceptability.

In at least one embodiment, at least the following functions can be realized with the operating device:

acquiring patient data of the patient from at least one acquisition-user interface, selecting, via at least one selection user interface, a medical technology protocol containing operating parameters which is to be carried out for the acquired patient, adjusting remotely-adjustable components of the medical apparatus on the patient positioned in the medical apparatus and the medical technology protocol to be carried out using at least one adjustment user interface, and triggering the medical technology procedure with the patient positioned and the components adjusted in at least one triggering user interface.

In addition, all the statements made in the aforementioned subsequently published EP 17202205.5 are also to be applied in the context of this disclosure as EP 17202205.5 is incorporated herein by reference, in its entirety and for all purposes.

The operating device which, in a particularly preferred embodiment is a smart device, therefore in particular, a smart phone and/or a tablet as is commercially available, has a touch screen on which various different steps/functions of the medical apparatus workflow which implements the examination and/or treatment process on the patient, associated user interfaces can be displayed and offer corresponding input possibilities. For this purpose, the operating device has, in particular, a control unit on which, at least partially, a control computer program runs, in particular, as an app.

Furthermore, the operating device preferably has a radio interface so that it is configured for wireless communication with a control unit of the medical apparatus, wherein the control unit of the operating device and the control unit of the medical apparatus can cooperate as a control apparatus in order to realize various aspects of the method according to the invention, which are described in greater detail below. In particular, it enables the communication connection between the control unit of the medical apparatus and the control unit of the operating device via corresponding radio interfaces, firstly to transfer control information generated from user inputs to the control unit of the medical apparatus in order to implement it accordingly, and/or secondly to provide feedback information and/or status information from the control unit of the medical apparatus to the control unit of the operating device in order to represent this information accordingly and/or to evaluate it for the operation of the operating device. The representation can take place accordingly via the user interface. Further information connections can naturally also exist, as already mentioned, for example, to an information system (RIS/HIS).

Thereby, the medical apparatus can be implemented, in particular, as an imaging X-ray apparatus so that, in particular, the complete medical apparatus workflow of an X-ray examination can be implemented via the operating device. In an operating concept accompanying the entire medical apparatus workflow, via a suitable, skillful design of the different user interfaces on the touch screen, a complete operation of the medical apparatus directly from the hand of the operator is possible and the necessity of multiple changes of operating location and/or operating apparatus no longer exists. The present invention even permits, with such an operating concept, for an anteroom for controlling the medical apparatus to be dispensed with, wherein it can be provided with an X-ray apparatus that a radiation shielding wall is made available in the examination room.

For training the analysis algorithm, a deep learning method is preferably used. Since the analysis algorithm is to map complex situations and is to handle usefully a plurality of operational situations, the deep learning methods in which the inner structure of the analysis algorithm can also be trained suggest themselves, in particular, in order to create the highest possible quality artificial intelligence environment delivering prediction data.

In a particularly preferred development of at least one embodiment of the invention, during the use of the operating device, operating data describing the operating action of the operator is recorded and is assigned to current input data, wherein the training data thereby obtained is used for further training of the analysis algorithm. This means, therefore, that the analysis algorithm is constantly further trained through its use so that the quality of the prediction data can be lastingly and continuously increased, in order to achieve an excellent prediction quality and to offer to the operator in as many situations as possible exactly the user interface that he desires in the current operational situation. It is also monitored thereby, in particular, whether the operator changes the selected and/or adapted user interface once it has been shown to him in accordance with the method, changes it and uses instead another or a differently adapted user interface which can be used as the correct basic truth for this case in order to generate training data and further to improve the analysis algorithm.

In this context, but also generally, it is particularly advantageous if the operator is identified, in particular, at least at the start of his operating activity, wherein a user-specific analysis algorithm is used and/or the identity of the operator is taken into account in the selection and/or adaptation of the user interface. This means that the method described above can also be assigned to specific operators in that either the analysis algorithm is trained in an operator-specific manner, for example, also in an updating manner by generating training data and also described during daily operation, or the current operator can be taken into account at least during the selection and/or adaptation of the user interface, in that here, for example, preferences which can be stored in the user profile are also taken into consideration. In this way, idiosynchrasies of particular operators can be considered.

In a suitable development, the workflow data of at least partly already completed workflow steps of the medical apparatus workflow can be determined descriptively. This means that the workflow data can display a current position in the current medical apparatus workflow, which represents a substantial useful item of information in the selection of the correct, required user interface. For example, in phases in which the medical apparatus is just being adjusted to the patient, user interfaces can be largely excluded with regard to already completed workflow steps or at least regarded as improbable, while the completion of particular as yet incomplete workflow steps requiring further workflow steps and associated user interfaces can also be largely excluded.

In a particularly suitable development of the method according to at least one embodiment of the invention, it can be provided that the selection and display of a user interface takes place triggered by a trigger signal indicating a placement in a utilization position. For example, it can therefore be monitored constantly, in particular, on the basis of a sensor system of the operating device itself, whether the operating device is brought into a utilization position, for example, lying flat in the hand of the operator with the touchscreen facing the eyes of the operator. Such a placement in a utilization position takes place, for example, when the previously laid down operating device is taken up by the operator and is held so that a useful actuation in the user interface would be possible.

With an operating device already held in the hand also, corresponding movements/position changes can be observed in order to ascertain the creation of the utilization position. The assumption of the utilization position from a non-utilization position denotes the desire of the operator to use the operating device and therefore represents an excellent trigger signal for determining prediction data and for selecting and/or adapting a user interface, so that the operator receives the necessary information and/or the necessary functionality provided directly. It should be noted thereby that other trigger signals are naturally, in principle, also conceivable, in particular, those which are generated by actuation of a corresponding supporting operating element in a user interface that has just been displayed, for example, if the user himself requests current intelligent, targeted support during operation. Such a supporting operating element can preferably be provided in all the user interfaces displayed.

For determining a trigger signal indicating a placement in a utilization position, it can be provided that the trigger signal is determined by evaluating position data indicating the position of the operating device and/or movement data indicating the movement of the operating device. Similarly to the part of the position data forming the input data, it is herein particularly preferred if, for determining the position data and/or the movement data, operating device sensors of the operating device itself are at least partially used.

In one embodiment of the operating device as a smart device, it is herein particularly preferred if the operating device sensors normally already provided there are used. For example, the operating device configured, in particular, as a smart device can have at least one operating device sensor recording sensor data describing the movement and/or the position of the operating device at least in the room in which the medical apparatus is situated, wherein position data describing the position and the orientation of the operating device and/or a movement of the operating device is determined from the sensor data and taken into account during the determination of the trigger signal and/or as input data.

A concrete embodiment provides in this regard that the operating device configured, in particular, as a smart device has at least one operating device sensor recording sensor data describing the movement and/or the position of the operating device in the room in which the medical apparatus is situated, wherein position data describing the position and the orientation of the operating device relative to components of the medical apparatus that are to be adjusted and/or movement data describing a movement relative to the components is determined from the sensor data and taken into account as input data during the determination of the prediction data. Such information provides, in particular, indications regarding the selection of at least one of the components for adjustment/use. Preferably, an evaluation can also take place for determining an operator input in relation to at least one of the components. Herein, particularly advantageously, the sensor system already present in the smart device can be used to enable a complete orientation and position recognition (and therefore also a movement recognition) of the smart device in the room in which the medical apparatus is situated.

The medical apparatus preferably has device(s) for defining current adjustment information of the components which describes their position in the room, as is known in principle, so that, for example, the system geometry can be just as well known in the control unit of the medical apparatus as the current setting of the actuators for moving/adjusting the components, which is determinable, for example, via the motor encoder or the corresponding sensors. Once the position of the medical apparatus in the room is also known, the relative positions and alignments and/or movements of the at least one component and of the smart device can therefore be determined and evaluated with regard to the remote operation of the components. It is thus in particular possible to point intuitively to components and/or for remote operation of components, to carry out corresponding movements with the smart device, so that an operation is possible conveniently and while looking at the components to be controlled. For this purpose, the operating device is preferably configured elongate, in particular, having a substantially rectangular and flat basic shape, so that the operating device can be directed toward components to be operated.

If a camera is used as the operating device sensor, optical markers arranged in the room, the position of which in the room is known, can be detected and used for determining the position data and/or the movement data. Active markers are also conceivable, for which a short-range radio connection can be established. The possibility for establishing such a short-range radio connection, in particular via Bluetooth/Bluetooth Low Energy or the properties thereof can also be evaluated in order to check the closeness of the operator to the components to be adjusted and, for example, to activate the corresponding adjustment user interface dependent thereon. Sensors other than cameras can naturally also be used as operating device sensors, for example, acceleration sensors and/or rotary speed sensors to realize dead reckoning navigation, in particular, in addition to a marker navigation, for example, if the latter is unavailable and/or must be plausibility checked.

In a particularly advantageous development of at least one embodiment of the present invention, it can be provided that the analysis algorithm is also configured for determining an item of error information as prediction data if mutually contradictory input data is used, wherein in the presence of an item of error information, an output describing the error information takes place in the user interface to be displayed. This means that the artificial intelligence analysis algorithm can also check the plausibility of the input data, in particular with regard to particular aspects that are to be excluded, for example, the use of components of the medical apparatus that are not suitable for a selected medical technology protocol and/or the patient and suchlike.

If, for example, a medical technology protocol is selected in which the patient is to be positioned on a patient support and examined with an X-ray apparatus as the medical apparatus, but the position data indicates that the patient is standing in front of a Bucky wall stand and also where the operator with the operating device is situated, an error can be assumed and a corresponding indication can be output to the operator, for example, that the patient is to be examined not with the Bucky wall stand, but using the patient support. Naturally, other contradictions, for example, adjustments to incorrect examination and/or treatment regions of a patient can also be monitored, wherein accordingly, the user interface can then immediately be selected for the correct adjustment of the corresponding component of the medical apparatus and, for example, can be adapted for the additional output of the error information. In this way, errors during the examination and/or treatment process of the patient can be prevented.

In a so-called "weakened form", such an error correction can also result by way of the usual functional manner of the analysis algorithm proposed here once, for example, the analysis of the relative position of the patient and of relevant components of the medical apparatus give indications as to whether and which components have still to be adjusted. If, for example, the collimator is still not adjusted according to the selected medical technology protocol during an X-ray examination, it can be anticipated that the operator will do this next and the corresponding user interface will be displayed.

On the other hand, the display of the corresponding user interface naturally leads thereto that the operator scrutinizes and corrects or improves a possibly already undertaken adjustment when this appears suitable for increasing the quality of the examination process and/or the treatment process. In particular, a corresponding item of information can be represented with the user interface, for example, a currently provided accuracy of an adjustment. In this way, the procedure according to the invention also leads to an improvement in the quality of the examination and/or treatment procedure.

In addition to the method, at least one embodiment of the invention also relates to a wireless handheld, mobile operating device for controlling a medical apparatus, having a touch screen and a control unit configured for carrying out the method according to the invention. The execution of the method according to the invention can, however, also be distributed, so that the invention also relates to an operating system for controlling the operation of a medical apparatus, having a wireless handheld, mobile operating device with a touch screen and a control apparatus comprising a control unit of the operating device and a control unit of the medical apparatus configured for carrying out the method according to the invention. All the disclosures relating to the method according to embodiments of the invention can be transferred similarly to the operating device according to embodiments of the invention and the operating system according to embodiments of the invention, so that the aforementioned advantages can also be obtained with this.

Finally, at least one embodiment of the invention also relates to a medical apparatus, in particular, an imaging apparatus having an operating device according to at least one embodiment of the invention or an operating system according to at least one embodiment of the invention. The above disclosures can also naturally be applied to the medical apparatus.

The medical apparatus can be configured, in particular, as an imaging X-ray apparatus which comprises a radiation shielding wall in a room in which it is arranged. In particular if, on the basis of an integral operating concept, an anteroom for controlling the medical apparatus is dispensed with, it is suitable in medical apparatuses using radiation, in particular, X-ray apparatuses, to use a radiation shielding wall in the actual examination room.

A computer program according to at least one embodiment of the invention is, for example, directly loadable into a memory store of a control unit of an operating device or a control apparatus of an operating system and has program segments in order to carry out the steps of a method according to at least one embodiment of the invention when the computer program is executed in the control unit of the operating device or the control apparatus of the operating system.

The computer program can be stored on an electronically readable data carrier according to at least one embodiment of the invention which therefore comprises electronically readable control information stored thereon, which comprises at least one computer program according to at least one embodiment of the invention and is configured such that, on use of the data carrier in a control unit of an operating device or a control apparatus of an operating system, the control information carries out a method according to at least one embodiment of the invention. The electronically readable data carrier can be, in particular, a non-transient data carrier, for example, a CD-ROM.

FIG. 1 shows a sketch of the principle of an example embodiment of a medical apparatus 1 according to the invention which is arranged in a room 2 and is configured here as an X-ray apparatus. The medical apparatus 1 has a plurality of adjustable components 3 which can be movable, for example, by remote operation. The components 3 can comprise, for example, an X-ray source, an X-ray detector, a collimator apparatus and a patient table. The operation of the medical apparatus 2 is controlled by a control unit 4.

As an operating device of the medical apparatus 1, here a wireless handheld, mobile operating device 5 configured as a smart device, specifically a smart phone, is provided, the control unit 6 of which can establish a wireless communication connection 7 to the control device 4 via a corresponding radio interface (not shown in detail here), in particular a Bluetooth interface and/or preferably a WLAN interface. The Bluetooth interface, wherein here Bluetooth Low Energy (BLE) is used, is otherwise also used to establish short-range radio connections 8 to at least a portion of optical markers 9, in concrete terms, at least to active optical markers 9 which therefore can be controlled for the output of optical signals that are to be detected. The markers 9 can also be pure BLE markers or BLE beacons.

The operating device 5 further comprises, as is known in principle, a touch screen 10 as an operating means and display. Furthermore, the operating device 5 has operating device sensors 11, in the present case two cameras, specifically a front camera and a rear camera, acceleration sensors, rotary speed sensors and a magnetic field sensor which acts as a compass.

Actuators 12 drivable by the control unit 4 for providing the adjustability, for example motors, are assigned to the adjustable components 3, the actuators otherwise also feeding their respective position back to the control device 4, so that it constantly knows the adjustments, in particular, positions of the components 3 due to the system geometry of the medical apparatus 1 which is also known to it. The control unit 4 also knows the position of the medical apparatus 1 in the room 2. This makes it possible, in particular, given a known position and orientation or a known movement of the operating device 5 in the room 2 as corresponding position data or movement data, to place these in relation to the respective components 3, so that adjustments of these components 3 can be undertaken via the operating device 5. In particular, via the operating device 5, one component 3 can be selected for adjustment and, via the operating device 5 by way of the movement thereof, a specification for adjustment can be given.

Position data and/or movement data of the operating device 5 in the room 2 and also outside the room 2 can be utilized in the context of the present invention, that is in particular, during a medical apparatus workflow for carrying out an examination procedure on a patient, as input data of an analysis algorithm. In order to determine the position data and the movement data, therefore the orientation, position and also movement of the operating device 5, the markers 9 which are detectable by the cameras are at least partially used in the space 2. This is described below with reference to FIG. 2.

Figure 2:
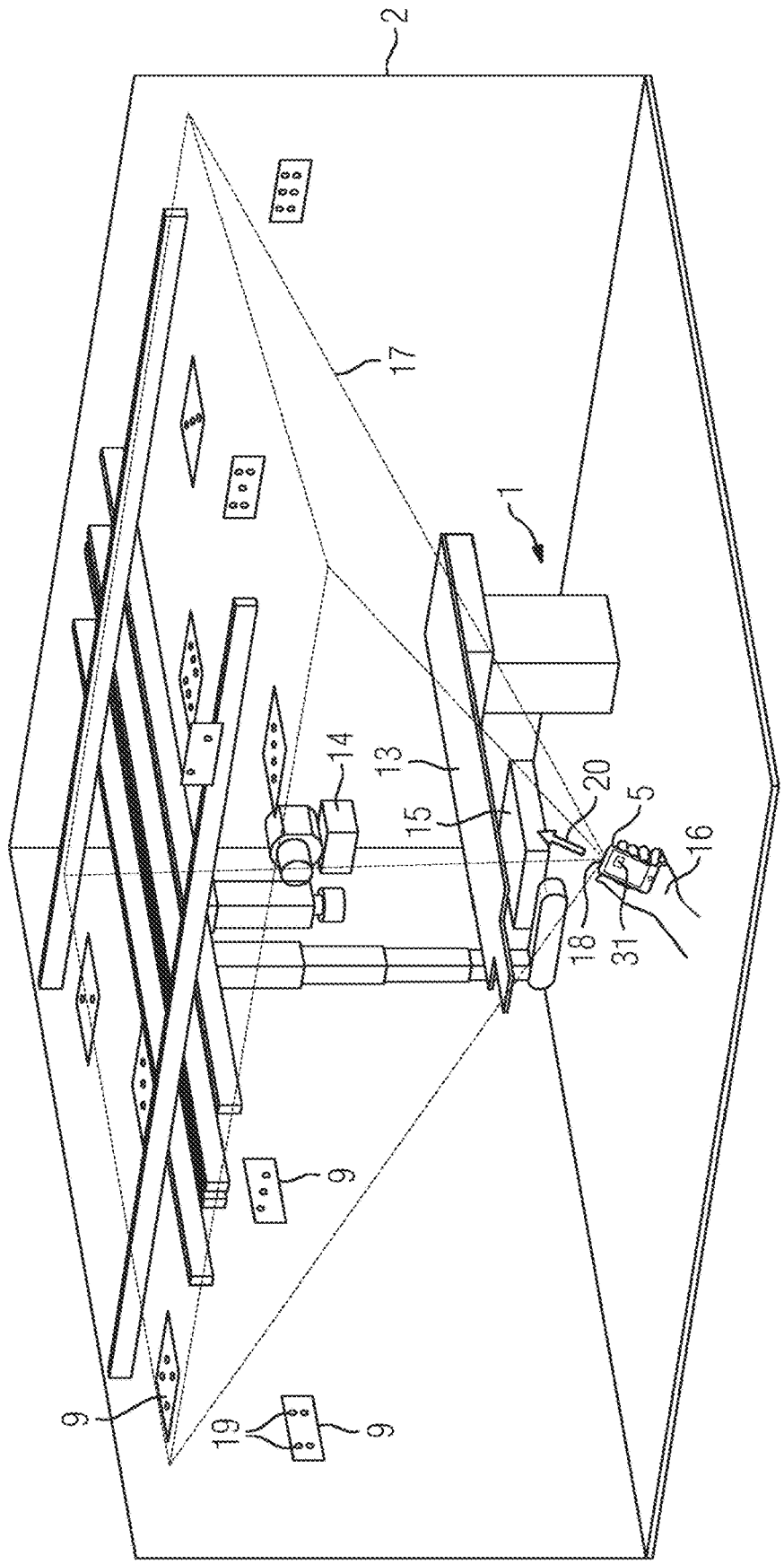
FIG. 2 is a representation to illustrate a localization via markers and a camera of an operating device.

FIG. 2 shows a perspective view of the room 2. Visible firstly are the medical apparatus 1 with the patient table 13, the X-ray radiator 14 and the X-ray detector 15 as components 3. The collimator apparatus (not shown in detail for the sake of clarity) is realized in the structural unit with the X-ray radiator 14. A hand 16 of an operator holds the operating device 5 in the room 2, wherein the detection region 17 of the front camera 18 is indicated as the operating device sensor 11. The markers 9 clearly distinguishable in their optically perceptible patterns are visible at different positions in the space 2, in the present case for the sake of clarity, distributed at least on the ceiling and the walls; an arrangement of optical markers 9 on the floor is naturally also possible. The active markers 9 here have infrared LEDs 19 in different patterns.

Since the smart device 5 is flat and elongate, lying in the hand 16 it has a clearly defined pointing direction 20, symbolized by an arrow, specifically the extension of the longitudinal axis of the operating device 5.

At least when the operating device 5 is situated in the room 2, the markers 9 are at least partially used in order to determine highly precise position data and movement data of the operating device 5, which occurs continuously in the control unit 4 and/or the control unit 6. If the markers 9 are not or insufficiently detectable, for example, because the operating device 5 is situated outside the room 2, nevertheless via external sensors, other markers, radio-based position determinations and the like, position data and/or movement data can be determined, wherein movement data can be determined also and/or exclusively from data of the acceleration sensors and/or rotary speed sensors. These further determining possibilities can also be used in general, alternatively to optical markers 9.

Once the position and the properties of the markers 9 have been determined in a configuration phase, these are then stored and available, for example, in a database. The markers 9 detected by the camera 18 can therefore serve for position determination, wherein the active markers 9 are controlled via the corresponding short-range radio connections 8, in synchronization with the operating device 5, to emit corresponding detectable signals. The infrared LEDs 19 enable a reliable recognition of the markers 9. On the basis of the short-range radio connection 8, the active markers 9 also act as radio beacons, which enables at least a rough position determination (with transit time and field strength measurements). Such a coarse position determination could also be achieved with optical markers emitting active light and operating by modulation of an identification signal, acting as light beacons. In support of the sensor data of the camera, the sensor data of the acceleration sensors (tilting in the room), of the rotary speed sensors (movement) and of the magnetic field sensors (alignment relative to north roughly determinable) are also taken into account.

As FIG. 1 also shows, in addition to the medical apparatus (or as part of the same), also provided in the room 2 is a radiation shielding wall 21, behind which an operator can stand whenever radiation is released.

An intelligent, adaptive user interface can be realized on the touch screen 10 of the operating device 5. For this purpose, an artificial intelligence analysis algorithm running on the control unit 6 and/or the control unit 4 and which analyzes the current operational situation and seeks to predict which functionalities and/or information of the operator is needed next, can be used. This is described below with reference to FIG. 3.

FIG. 3 shows on its right-hand side the region of the "situation awareness" in which the operational situation is mapped with input data 22. The input data 22 comprises at least patient data 23 relating to the current patient, operational status data 24 relating to the operational status of the medical apparatus 1, the position data 25 describing the position of the operating device 5 and of the patient in relation to the medical apparatus 1 and the medical apparatus workflow and workflow data describing a current position in the medical apparatus workflow. Further input data 22 can also be used, for example, the movement data relating to the operating device 5, as already described above with regard to FIGS. 1 and 2.

The input data 22 is fed to the analysis algorithm 27 of the artificial intelligence which has been trained by way of a deep learning method and, otherwise, also continuously further trained once actual operating actions by the operator can be constantly recorded as a basic truth for corresponding operational situations and can thus be used to improve the quality of the analysis algorithm 27.

The analysis algorithm 27 finally predicts which operating action is most likely to be undertaken next by the operator and/or which information of the operator is most likely to be needed. This prediction data 28 can however additionally contain error information 29 if the analysis algorithm 27 ascertains that input data 22 items contradict one another so that therefore a plausibility check of the operational situation is also carried out. If, for example, it is ascertained that the patient is wrongly positioned for a selected specific X-ray examination, the corresponding workflow data items and the operational status data of the medical apparatus together with the position data 25 of the patient contradict one another, which can be contained as error information 29 in the prediction data and can lead to a corresponding adaptation of the user interface to be displayed, in particular, an extension by the error information 29. The selection can also be influenced by the error information 29, for example, in that the user interface in which the error can be corrected is immediately offered to the operator.

In a step 30, the selection and/or adaptation of the user interface to be displayed then takes place, which provides the functionalities most probably needed by the operator or the information most probably needed by the operator and, possibly also orients itself to the error information 29 or absorbs it. The user interface thus determined is displayed on the touch screen 10 of the operating device 5.

The process of the intelligent, adaptive determination of a user interface described in relation to FIG. 3 on the basis of the selection algorithm 27 of the artificial intelligence can be triggered by a trigger signal. Thereby, via the control unit 4 and/or the control unit 6, in particular, by evaluating the position data 25 of the operating device 5 and/or the movement data of the operating device 5 it is checked whether a placement of the operating device 5 into a utilization position takes place. A utilization position of this type can be provided by holding the operating device 5 in the hand 16 such that the touch screen 10 is oriented toward the eyes of the operator. The placement into the utilization position indicates that the operator wishes to use the operating device 5. For this, on the basis of the procedures described by reference to FIG. 3, he immediately receives a suitable user interface.

In the example embodiment described here, support can also be requested by the analysis algorithm 27 from each user interface via a supporting operating element 31 indicated in FIG. 2 which is mapped accordingly on the touch screen and can be actuated by the operator in order similarly to output a trigger signal for the use of the analysis algorithm.

It should be noted at this point that the analysis algorithm 27 or the selection and/or adaptation of the user interface in the step 30 can also take place in a user-specific manner, wherein the operator is preferably identified at the start of his operating activity.

FIGS. 4 to 8 show different example operational situations schematically and the corresponding selection and/or adaptation of the user interface. Thereby, the room 2 is again shown in all situations with the medical apparatus 1 which, in the present case otherwise in addition to the patient table 13, also has a Bucky wall stand 32, which can alternatively be used. Shown schematically is also a waiting room 33 adjoining the room 2. The operator has the reference sign 34 and the patient has the reference sign 35. Furthermore, cameras 36 are also shown within the room 2, which, as sensors, can also provide input data.

In the operational situation of FIG. 4, via an acquisition user interface, the patient 35 and thus the patient data 23 of the patient have already been acquired. Via a selection user interface, a medical technology protocol containing operating parameters which is to be carried out for the patient 35 has already been selected. A pre-positioning of components 3 of the medical apparatus 1 can optionally also have taken place already. The patient 35 is obviously already situated in the room 2 and has been led by the operator 34 to the Bucky wall stand 32. The operator has also already positioned the patient 35 at the Bucky wall stand 32. The position data of the patient and of the operating device 5 show that the operator 34 and the patient 35 are positioned close to the Bucky wall stand 32. The operator 34 has just placed the operating device 5 in a utilization position.

On the basis of the corresponding input data 22, the analysis algorithm 27 ascertains that either the fine adjustment of the height of the Bucky wall stand 32 or the collimation can be a next step. If the input data 22 now shows that the patient height, for example, scanned by the camera 36, indicates that the position of the Bucky wall stand 32 and of the X-ray radiator 14 is too low, it is most probable that a height adjustment is to take place via the operating device 5, so that the corresponding user interface is shown. If, however, it is determined that the patient height, the position of the Bucky wall stand 32 and the position of the X-ray radiator 14 have been correctly selected, it is assumed that the collimation should be set and a corresponding user interface is shown on the touch screen 10 of the operating device 5.

With regard to the error information 29, it should be noted that, for example, it can be generated when the selected medical technology protocol shows that the patient 35 is actually to be examined using the patient table 13.

Figure 5:
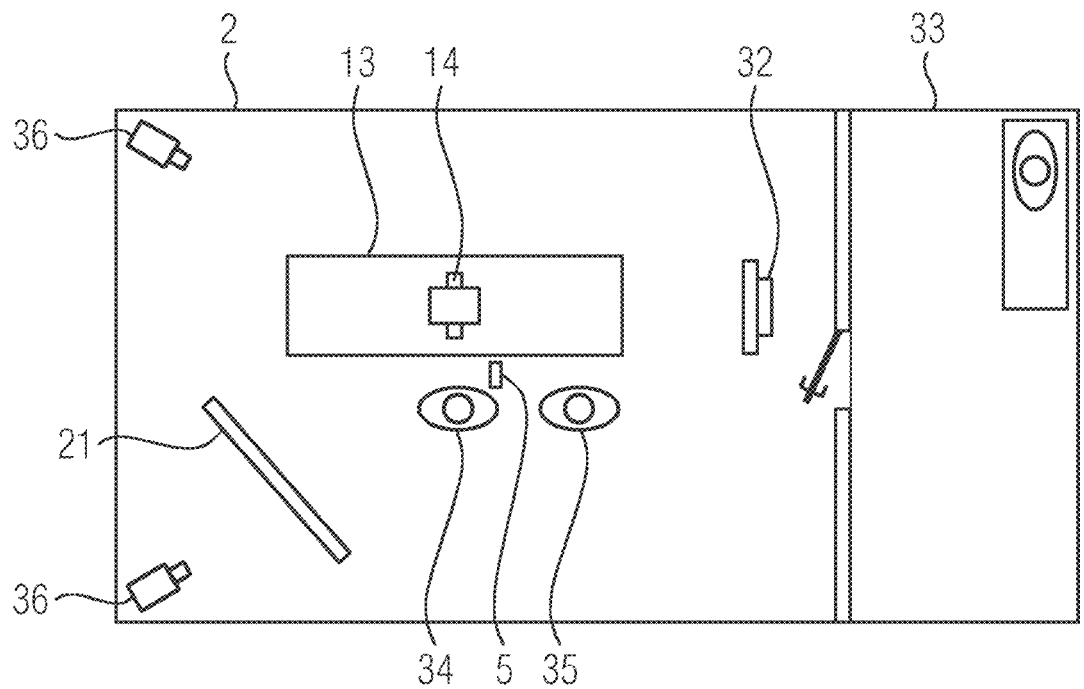
FIG. 5 is a second operational situation.

FIG. 5 shows a comparable scenario, only that the patient 35 is to be examined on the patient table 13 and has already been brought thereto. Once the next step is now the adjustment of the patient table 13, a corresponding user interface for adjusting the patient table 13 is also selected and displayed, according to the determined prediction data 28.

Figure 6:
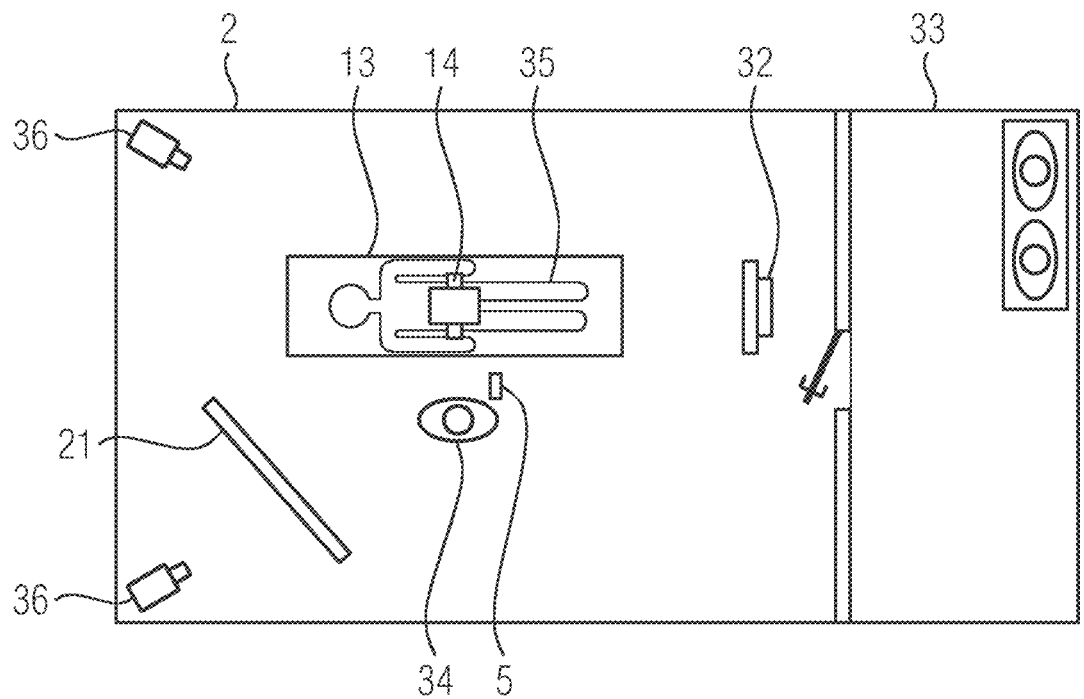
FIG. 6 is a third operational situation.
Figure 7:
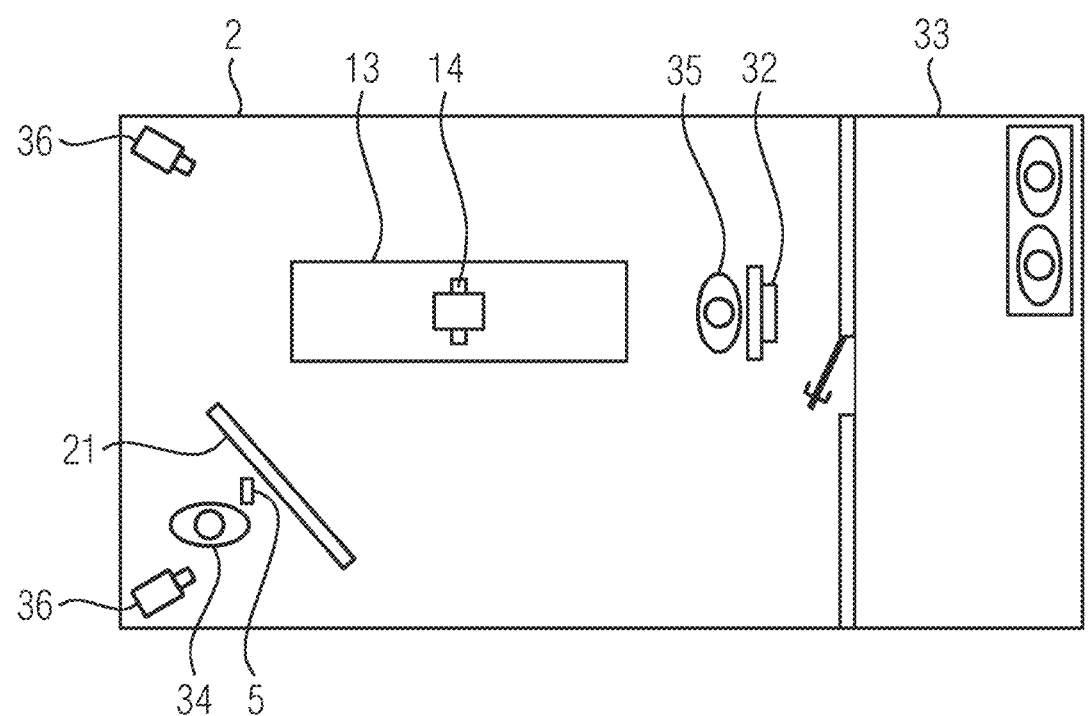
FIG. 7 is a fourth operational situation.

In FIG. 6, the patient 35 is already positioned on the patient table 13. If the analysis algorithm 27 ascertains in this situation, for example, that the patient 35 is taller/shorter than the average patient, an adaptation of operating parameters describing the strength of the radiation can be recommended in that a corresponding user interface is displayed on the touch screen 10 of the operating device 5. Otherwise, the information can be displayed that everything is ready for recording an X-ray image and the user 34 should place himself behind the radiation shielding wall 21.

In the operational situation in FIG. 7 which again relates to the operational situation in FIG. 4, the patient 35 is correctly positioned in front of the Bucky wall stand 32 and the user 34 is situated behind the radiation shielding wall 21. Once it becomes known, on the basis of the workflow data 26, that all the previous steps as far as collimation are successfully completed and the user 34 is also situated behind the radiation shielding wall 21, a corresponding triggering user interface can be selected and displayed on the touch screen 10 of the operating device 5.

If, however it is ascertained that the operator 34 is situated behind the radiation shielding wall 21 without the patient 35 having been positioned or without collimation taking place or without a patient 35 being present at all, the selected and/or adapted user interface has a different appearance and depends upon other input data/system conditions, so that, for example, a patient list, an examination list or a preliminary image viewing of the last recording can be displayed on the operating device 5.

Figure 8:
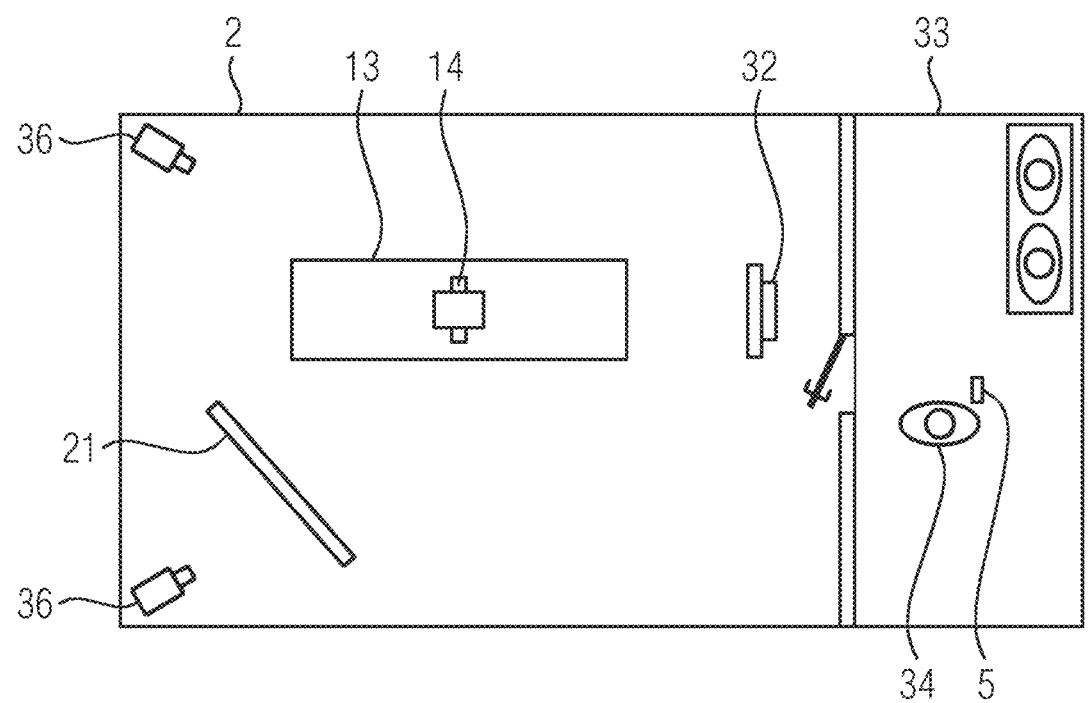
FIG. 8 is a fifth operational situation.

FIG. 8 shows, finally, a situation in which the operator 34 is not situated in the room 2, but in the room 33. The previous examination procedure is completed. If a new patient 35 has already been selected, a selection user interface for selecting a medical technology protocol is displayed on the touch screen 10 of the operating device 5; if no new patient 35 has yet been selected, a patient list and/or an acquisition user interface can be displayed; if no patients are available in the patient list, a general user interface or a corresponding information item can be displayed in a user interface on the touch screen 10 of the operating device 5.

Although the invention has been illustrated and described in detail with the preferred example embodiment, the invention is not restricted by the examples disclosed and other variations can be derived therefrom by a person skilled in the art without departing from the protective scope of the invention.

REFERENCE SIGNS

1 Medical apparatus
2 Room
3 Component
4 Control unit
5 Mobile operating device
6 Control unit
7 Wireless communication connection
8 Short-range radio connection
9 Marker
10 Touch screen
11 Operating device sensor
12 Actuator
13 Patient table
14 X-ray radiator
15 X-ray detector
16 Hand
17 Detection region
18 Camera
19 Infrared LED
20 Pointing direction
21 Radiation shielding wall
22 Input data
23 Patient data
24 Operational status data
25 Position data
26 Workflow data
27 Analysis algorithm
28 Prediction data
29 Error information
30 Step
31 Operating element
32 Bucky wall stand
33 Waiting room
34 Operator
35 Patient
36 Camera

The invention claimed is:

1. A method for controlling the operation of a medical apparatus via a wireless, handheld mobile operating device including a touch screen, with a plurality of functions of a medical apparatus workflow being realized via the wireless, handheld mobile operating devices for at least one of an examination and a treatment process of a patient with the medical apparatus, the method comprising:
   determining input data describing a current operational situation, the input data including patient data relating to the patient, operational status data relating to operational status of the medical apparatus, position data describing position of at least one of the wireless, handheld mobile operating device and the patient in relation to the medical apparatus, and workflow data describing at least one of a medical apparatus workflow and a current position in the medical apparatus workflow;
   determining, using an artificial intelligence analysis algorithm, at least one of a subsequent operating action of an operator of the wireless, handheld mobile operating device and prediction data describing an item of information needed next by the operator; and
   at least one of selecting the user interface to be displayed and adapting the user interface to be displayed, based upon the prediction data and then displaying the user interface after being at least one of selected and adapted, wherein the workflow data of at least partly already completed workflow steps of the medical apparatus workflow, are determined descriptively.

2. The method of claim 1, wherein, a deep learning method is used for training the artificial intelligence analysis algorithm.

3. The method of claim 2, wherein, during the use of the wireless, handheld mobile operating device, operating data describing operating actions of the operator is recorded as training data and is assigned to current input data, and wherein the training data is used for further training of the artificial intelligence analysis algorithm.

4. The method of claim 2, wherein the operator is identified, and wherein at least one of a user-specific analysis algorithm is used and an identity of the operator is taken into account, in the at least one of the selecting and adapting of the user interface.

5. The method of claim 2, wherein the selecting and display of a user interface takes place triggered by a trigger signal indicating a placement of the wireless, handheld mobile operating device in a utilization position.

6. The method of claim 5, wherein the trigger signal is determined by evaluating position data indicating at least one of the position of the wireless, handheld mobile operating device and movement data indicating the movement of the wireless, handheld mobile operating device.

7. The method of claim 1, wherein, during the use of the wireless, handheld mobile operating device, operating data describing operating actions of the operator is recorded as training data and is assigned to current input data, and wherein the training data is used for further training of the artificial intelligence analysis algorithm.

8. The method of claim 1, wherein the operator is identified, and wherein at least one of a user-specific artificial intelligence analysis algorithm is used and an identity of the operator is taken into account, in the at least one of the selecting and adapting of the user interface.

9. The method of claim 1, wherein the selecting and display of a user interface takes place triggered by a trigger signal indicating a placement of the wireless, handheld mobile operating device in a utilization position.

10. The method of claim 9, wherein the trigger signal is determined by evaluating position data indicating at least one of the position of the wireless, handheld mobile operating device and movement data indicating the movement of the wireless, handheld mobile operating device.

11. The method of claim 1, wherein the artificial intelligence analysis algorithm is also configured for determining an item of error information as prediction data upon mutually contradictory input data being used, and wherein upon a presence of an item of error information being determined, an output describing the error information occurs in the user interface to be displayed.

12. The method of claim 1, wherein the medical apparatus is an imaging apparatus.

13. A wireless handheld, mobile operating device for controlling the operation of a medical apparatus comprising:
   a touch Screen; and
   a controller configured for:
      determining input data describing a current operational situation, the input data including patient data relating to the patient, operational status data relating to operational status of the medical apparatus, position data describing position of at least one of the wireless, handheld mobile operating device and the patient in relation to the medical apparatus, and workflow data describing at least one of a medical apparatus workflow and a current position in the medical apparatus workflow;
      determining, using an artificial intelligence analysis algorithm, at least one of a subsequent operating action of an operator of the wireless, handheld mobile operating device and prediction data describing an item of information needed next by the operator; and
      at least one of selecting the user interface to be displayed and adapting the user interface to be displayed, based upon the prediction data and then displaying the user interface after being at least one of selected and adapted, wherein the workflow data of at least partly already completed workflow steps of the medical apparatus workflow, are determined descriptively.

14. An operating system for controlling the operation of a medical apparatus including the wireless handheld, mobile operating device of claim 13, comprising:
   a controller of the wireless handheld, mobile operating device; and
   a controller of the medical apparatus.

15. A medical apparatus, comprising the operating system of claim 14.

16. A non-transitory computer program product, storing a computer program to carry out the method of claim 1 when executed on a controller of a wireless handheld, mobile operating device.

17. A non-transitory electronically readable data carrier storing a computer program to carry out the method of claim 1 when executed on a controller of an operating system for controlling the operation of a medical apparatus.

* * * * *